United States Patent [19]

Craig

[11] Patent Number: 5,492,841

[45] Date of Patent: Feb. 20, 1996

[54] QUATERNARY AMMONIUM IMMUNOGENIC CONJUGATES AND IMMUNOASSAY REAGENTS

[75] Inventor: Alan R. Craig, Wilmington, Del.

[73] Assignee: E. I. Du Pont de Nemours and Company, Wilmington, Del.

[21] Appl. No.: 199,380

[22] Filed: Feb. 18, 1994

[51] Int. Cl.⁶ .................... C07K 14/765; G01N 33/546
[52] U.S. Cl. .................... 436/534; 435/7.94; 435/188; 436/533; 436/816; 530/404; 530/405; 530/807
[58] Field of Search .................... 530/807, 404, 530/405, 389.8; 436/533, 534, 816; 435/7.94, 188

[56] References Cited

U.S. PATENT DOCUMENTS

| | | | |
|---|---|---|---|
| 3,682,634 | 8/1972 | Willems | 96/29 |
| 3,709,808 | 1/1973 | Spector | 260/121 |
| 3,852,157 | 12/1974 | Rubenstein et al. | 195/63 |
| 4,025,501 | 5/1977 | Leute | 260/121 |
| 4,064,228 | 12/1977 | Gross | 424/1 |
| 4,078,049 | 3/1978 | Felix et al. | 424/1 |
| 4,104,367 | 8/1978 | Gomez et al. | 424/1 |
| 4,123,431 | 10/1978 | Soffer et al. | 260/292 |
| 4,281,065 | 7/1981 | Lin et al. | 435/188 |
| 4,490,473 | 12/1984 | Brunhouse | 436/518 |
| 4,939,264 | 7/1990 | Heiman et al. | 436/537 |
| 5,155,166 | 10/1992 | Danielson et al. | 525/54.1 |
| 5,157,123 | 10/1992 | Zara et al. | 546/291 |

FOREIGN PATENT DOCUMENTS

| | | |
|---|---|---|
| 0191536A1 | 2/1986 | European Pat. Off. . |
| 0264797A2 | 10/1987 | European Pat. Off. . |
| 0359063A2 | 9/1989 | European Pat. Off. . |
| 2561660 | 3/1984 | France . |
| 2-69196 | 9/1988 | Japan . |

OTHER PUBLICATIONS

M. Pallardy et al., Int. J. Immunopharmac, vol. 9, No. 2, pp. 151–156 (1987).
G. Alberici et al., J. Allergy and Clinical Immunology, vol. 77, No. 4, pp. 624–630 (1986).
R. Glockshuber et al., Biochemistry, vol. 30, pp. 3049–3054 (1991).
L. Krausz et al., Immunochemistry, vol. 13, pp. 51–57 (1976).
R. Rein et al., Comput. Chem. Res. Educ., Proc. Int. Conf. , vol. 2, Jul. 1971–Apr. 1994 (1973).
K. Soo Nam et al., Biochimica et Biophysica Acta, vol. 1046, pp. 89–96 (1990).
K. Schallreuter et al., Biochem. Biophys. Res. Comm, vol. 135, No. 1, pp. 221–227 (1986).
R. Schall et al., Clin. Chem., vol. 27, No. 7, pp. 1157–1164 (1981).

Primary Examiner—Mary E. Ceperley

[57] ABSTRACT

This invention relates to novel quaternary ammonium immunogenic conjugates and reporter reagents useful for eliciting antibodies and in immunoassays. Processes for preparing such quaternary ammonium immunogenic conjugates and their use in immunoassays and in eliciting antibodies are also disclosed.

10 Claims, No Drawings

QUATERNARY AMMONIUM IMMUNOGENIC CONJUGATES AND IMMUNOASSAY REAGENTS

TECHNICAL FIELD

This invention relates to novel immunogenic conjugates and immunoassay reagents, and more particularly, to quaternary ammonium immunogenic conjugates and quaternary ammonium reporter reagents useful for eliciting antibodies and for performing immunoassays.

BACKGROUND OF THE INVENTION

Specific binding reactions, such as antibody-antigen interactions, have been used extensively in immunoassays to detect and/or quantify numerous analytes present in biological fluids. Immunoassays have been developed for the determination of polyvalent antigens as well as haptens.

Of particular interest for clinical diagnostic purposes are haptens belonging to various classes of drugs, including drugs of abuse. Examples of such drugs of abuse include amphetamines, barbiturates, benzodiazepams, cocaine, methadone, methaqualone, opiates, phencyclidine (PCP), propoxyphene, tetrahydro-cannabinol (THC), and compounds of related structures.

The preparation of antibodies useful in immunoassays for the determination of such haptens is complicated in that these relatively small molecules can act as epitopes but, by themselves, are generally incapable of eliciting an immune response. Thus, in order to obtain antibodies specific for particular haptens of interest it is often necessary to immunize an appropriate host animal with an immunogenic conjugate of the hapten of interest or a derivative thereof and a carrier. Various known carriers include poly(amino) acids such as proteins and polypeptides. Commonly employed carriers include keyhole limpit hemocyanin (KLH), bovine serum albumin (BSA), ovalbumin, and pumpkin seed globulin.

Immunogenic conjugates useful in eliciting antibodies against haptens, including haptens having an amine functionality, have been prepared by modifying or derivatizing a hapten of interest to contain a reactive group, such as a carboxyl group, to facilitate its binding with a functional group, such as an amine group, of an immunogenic carrier substance such as a protein.

French Patent No. 2561660, having a publication date of Mar. 26, 1984, issued to Geffard, discloses an immunogen against a hapten group which contains a choline unit, prepared by reacting an amine or carboxyl group of an antigenic molecule with a compound of the formula Y—X$_2$—CO—Z', where X$_2$ is an alkyl group, Z' is either an OH group or protective group, and Y is a functional group capable of reacting with an amine or carboxyl group of a macromolecule, followed by esterification of the resulting coupled compound with choline.

U.S. Pat. No. 4,490,473 issued to Brunhouse on Dec. 25, 1984, discloses N,N,N-trimethylammonium phenyl compounds conjugated to an antibody through an amino linkage of the antibody. These compounds are disclosed as reagents useful in sandwich assays.

U.S. Pat. No. 4,078,049 issued to Felix et al. on Mar. 7, 1978, discloses an antigen comprising 6-aminocaproic acid (2-trimethylaminoethyl) ester covalently bonded to an immunogenic carrier material through a peptide bond formed from the 6-amino group and carboxyl groups contained in the immunogenic carrier.

European Patent Appln. 0191536, Visser et al., having a publication date of Aug. 20, 1986 discloses immunogens comprising an antigenic determinant coupled to an amphiphilic adjuvant molecule, and optionally, free amphiphilic adjuvant molecules.

U.S. Pat. No. 3,709,868 issued to Spector, on Jan. 1, 1973, discloses the coupling of an opium alkaloid hapten to immunogenic carrier proteins through the carboxyl group of a carboxy lower alkyl derivative of the phenolic hydroxy group of the alkaloid with a free amino group in the protein, thereby yielding a covalent peptide bond to form an opium alkaloid antigen.

None of these references disclose a quaternary ammonium immunogenic conjugate prepared by coupling a hapten or derivative thereof to an immunogenic carrier by attaching a bifunctional linking group capable of binding to the carrier, to a tertiary amine group present in the hapten or derivative thereof.

Haptens or derivatives thereof can also be conjugated with non-immunogenic carriers such as reporters to provide reporter reagents useful in immunoassays. Conjugates of haptens and a solid phase, such as latex particles, can provide latex particle reagents which can be used in various known particle agglutination immunoassay formats. For example, U.S. Pat. No. 4,401,765 issued Aug. 30, 1983 to Craig et al. and U.S. Pat. No. 4,480,042 issued Oct. 30, 1984 to Craig et al. disclose high refractive index shell core polymer particle reagents comprising biological compounds of interest coupled to particles and the use of these particle reagents in light scattering particle agglutination or inhibition immunoassays.

Quaternary ammonium compounds can be prepared from tertiary amines using known methodology involving alkylation of the nitrogen atom. Alkylation can generally be achieved through reaction with an alkyl halide. The amine can be aliphatic or aromatic. Such quaternary ammonium compounds have the general formula, $[R_4N^+]X^-$, where $R_4$ represents four non-hydrogen substituent groups and X is a halide anion. See for example, Morrison R. T. and Boyd, R. N., Organic Chemistry, sixth edition, page 854, Prentice Hall Inc. (1992).

However, quaternary ammonium reporter reagents which are conjugates of reporters and reporters or derivatives thereof which have a tertiary amine functionality have not been previously disclosed.

SUMMARY OF THE INVENTION

The quaternary ammonium immunogenic conjugates and reporter reagents of the present invention offer significant advantages over known immunogenic conjugates and reporter reagents. The quaternary ammonium immunogenic conjugates of the present invention can be used to elicit antibodies against a broad spectrum of haptens including all haptens or derivatives thereof which contain a tertiary amine group, and the reporter reagents can be applied in a wide variety of immunoassay formats.

This invention relates to a quaternary ammonium conjugate useful in immunoassays and/or for eliciting antibodies, for determining the presence and/or or amount of a hapten in a test sample, the hapten having a tertiary amine group or capable of being derivatized to have a tertiary amine group, comprising compounds of the formula:

((Q⁺—L—Z)ₓM) B⁻ wherein $Q^+$ is a quaternary ammonium group, cyclic or acyclic, which comprises a tertiary amine functionality present either in the hapten or in a derivative thereof;

L is a linker comprising from 0 to 20 carbon atoms and heteroatoms, including not more than 6 heteroatoms, arranged in a straight or branched chain and/or containing ring structures, with no more than two heteroatoms linked in sequence;

—Z— is a residue group selected from the group consisting of —C=O—, —CH=, —N=N—, —NH—, —NHCH₃—, —NH—S=C—, —SO₂—, —O—C=O—, and —C=O—NH—NH₂—;

x is greater than or equal to 1;

M is a carrier; and $B^-$ is an anion.

Another aspect of the invention relates to a quaternary ammonium immunogenic conjugate useful in immunoassays and in eliciting antibodies, for determining the presence and/or amount of a hapten in a test sample, prepared by a process which comprises: coupling a quaternary ammonium hapten derivative to a carrier, wherein the quaternary ammonium hapten derivative is obtained by attaching a linking group having a reactive group which is capable of binding to the carrier, to a tertiary amine group present either in the hapten or in a derivative of the hapten, the linking group comprising from 0 to 40 carbon atoms and heteroatoms, including not more than 6 heteroatoms, arranged in a straight or branched chain and/or containing ring structures, with no more than two heteroatoms linked in sequence.

The invention further relates to an antibody raised against the immunogenic conjugates described above.

A further aspect of the invention relates to an immunoassay for detecting the presence and/or amount of a hapten comprising the steps of immobilizing the immunogenic conjugate of claim 2 on a solid phase followed by carrying out any known immunoassay protocol.

DETAILED DESCRIPTION OF THE INVENTION

This invention relates to quaternary ammonium conjugates useful in immunoassays and for eliciting antibodies. This invention further relates to antibodies either monoclonal or polyclonal, produced using such quaternary ammonium conjugates as immunogens. In addition the present invention relates to immunoassays utilizing such quaternary ammonium immunogenic conjugates.

The immunogenic conjugates of the present invention are quaternary ammonium compounds of the formula:

((Q⁺—L—Z)ₓM) B⁻ wherein $Q^+$ is a quaternary ammonium group, cyclic or acyclic, and which comprises a tertiary amine group present either in the hapten or in a derivative thereof;

L is a linker comprising from 0 to 20 carbon atoms and heteroatoms, including not more than 6 heteroatoms, arranged in a straight or branched chain and/or containing ring structures, with no more than two heteroatoms linked in sequence;

—Z— is a residue group selected from the group consisting of —C=O—, —CH=, —N=N—, —NH—, —NHCH₃—, —NH—S=C—, —SO₂—, —O—C=O—, and —C=O—NH—NH₂—;

x is greater than or equal to 1;

M is a carrier; and $B^-$ is an anion.

By "hapten" is meant any molecule which can act as an epitope but which is incapable by itself of eliciting an immune response. In order to elicit an appropriate antibody response, a hapten can be bound, typically via covalent linkage, to an immunogenic carrier to produce an immunogenic conjugate capable of eliciting antibodies specific for the hapten.

The hapten utilized in preparing the immunogenic conjugate of the present invention can be a tertiary amine (tertiary amine hapten) or it can be a hapten which is capable of being derivatized to have a tertiary amine functionality. Preferably, the hapten utilized in the present invention is a tertiary amine hapten not requiring derivatization. Examples of such tertiary amine haptens include structures belonging to various classes of drugs such as the various classes of drugs of abuse, including for example, cocaine, methadone, methaqualone, opiates, phencyclidines (PCP), and propoxyphenes, as well as other drugs such as quinidine, procanimide, N-acetyl procanimide (NAPA) and tricyclic amine antidepressants. Such classes of drugs include the named drug, e.g., cocaine, as well as related structures such as these shown in Table 1 below. Immunogenic conjugates synthesized using one of these tertiary amine haptens are preferred. Examples of haptens which can be derivatized to produce tertiary amines include drugs of abuse such as amphetamines and benzodiazepams. Such haptens typically contain amine groups which can be derivatized employing known methodology. The structures of a selection of haptens useful in preparing the immunogenic conjugates and reporter reagents of the present invention are shown in Table 1.

TABLE 1

Amphetamines and Related Structures

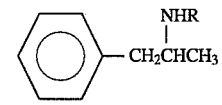

| | R |
|---|---|
| amphetamine | H |
| methadrine | CH₃ |
| Other: | |
| methylenedioxymethamphetamine | |

Benzodiazepams and Related Structures

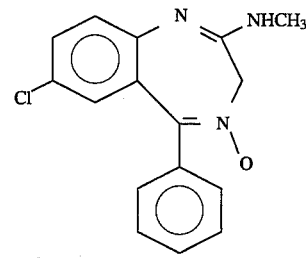

Chlorobenzodiazepoxide (librium)

Cocaine and Related Drugs

TABLE 1-continued cocaine benzoyl ecgonine ecgonine

Methadone and Related Structures methadone

Methaqualone and Related Structures

Structures Related to Methaqualone

Opiates and Related Structures opiate ring structure

| | R |
|---|---|
| codeine | $CH_3$ |
| morphine | H |

| | R |
|---|---|
| hydrocodone (dihidrocodeinone) | $CH_3$ |
| hydromorphone | H | levorphanol

TABLE 1-continued oxycodone

Phencyclidine

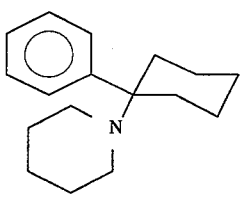

1-phenylcyclohexyl amine

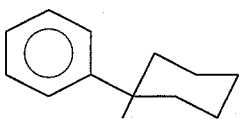

1-(1-phenylcyclohexyl)-4-hydroxypiperidine

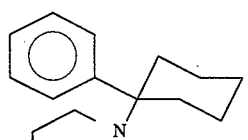

1-(3-hydroxy-1-phenylcyclohexyl)piperidine

Propoxyphene and Related Structures

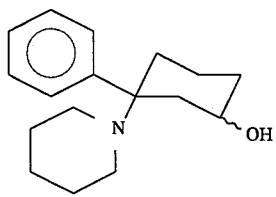

Structures Related to Propoxyphene

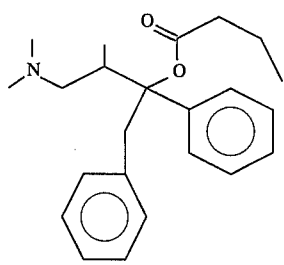

Quinidine and Related Compounds

TABLE 1-continued

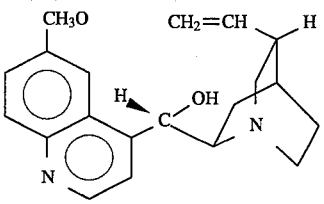

Tertiary amines can be produced through the known reaction generally referred to as alkylation of amines. This reaction is shown below:

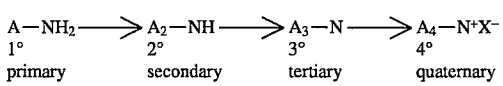

where A is a non-hydrogen substituent and X is the halide.

An amine can react with an alkyl derivative which is reactive with nucleophiles. The product is the amine of the next higher class. One of the hydrogens attached to the nitrogen is replaced by the alkyl group. The amine can be aliphatic or aromatic, primary (1°), secondary (2°), or tertiary (3°). The alkyl derivative can be straight-chained or branched, saturated or unsaturated, and can contain heteroatoms such as oxygen, sulfur, and nitrogen. The preferred alkyl derivative contains a straight chained group having from 1 to 10 carbon atoms. Useful derivatives include halides, preferably bromides and iodides and other good leaving groups such as toluene sulfonates.

The quaternary ammonium conjugates of the present invention can be prepared by coupling a tertiary amine hapten (or a hapten which has been derivatized to have a tertiary amine functionality) via a linking group suitable for linking to a carrier.

A tertiary amine hapten can be derivatized with a linking group using the alkylation reaction described above to produce a quaternary ammonium hapten having a positive charge balanced by some negative ion ($X^-$).

The linking group can be alkyl or aryl, straight chained or branched, and can contain carbon and heteroatoms. Linking groups suitable for binding to a carrier can contain reactive groups capable of reacting with the carrier so as to covalently bind the quaternary ammonium hapten derivative compound to the carrier. Examples of suitable reactive groups include —$CO_2H$, —$NH_2$, —NCO, —$CONHNH_2$, —CNOR, —CHO, —Br, —I, —NCS, —OCOCl, —$SO_2Cl$, —OCSCl, and —$NHCH_3$. The preferred linking group is a bifunctional linking group which group having from 1–20 atoms, and containing a —$CO_2$ reactive group for linking with the carrier; and a halide group for reacting with the tertiary amine of the hapten or derivative thereof.

The immunogenic conjugate can be linked with the quaternary ammonium hapten or hapten derivative by various linkages using the above described reactive groups, including for example, amide, imine, diazo, alkyl, urea, thiourea, carbamate and thiocarbamate linkages. The linker L and residue Z result from the reaction of the linking group with the carrier.

The preferred linker is an alkyl group having from 1 to 10 atoms. The residue Z results from the binding of the reactive group of the linking group of the quaternary ammonium hapten to the carrier.

Examples of suitable residue groups Z, include for example, C=O, C=NH, NH, NHCH$_3$, N=N, SO$_2$, and CH$_2$. The preferred residue group Z, is C=O, arising from the reaction of a carboxyl reactive group on the linking group with an amine group on a poly (amino)acid.

By "carrier" is meant: 1) any substance that can render the hapten capable of eliciting an immune response in an appropriate host animal and 2) any non-immunogenic substance which can be used as a reporter. Examples of carriers include various poly(amino)acids such as proteins, polypeptides, glycoproteins as well as carboyhdrates, yeasts polysaccharides and solid phases such as latex particles. Preferably the carrier is bovine serum albumin (BSA). Examples of other suitable carriers include hemocyanin, keyhole limpit hemocyanin (KLH), egg ovalbumin, bovine gamma globulin, synthetic poly (amino) acids having sufficient reactive groups. Preferably the carrier is linked to the linker via an amine group present in the carrier.

The subscript x can be any number greater than or equal to 1 and will vary depending on the linkage employed between the tertiary amine (via the linker) and the carrier. For example, if the reactive group or the linking group is carboxyl group, the number x will depend on the number of amine groups present in the carrier.

The preferred quaternary ammonium conjugate of the present invention is of the structure:

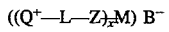

wherein Q is a quaternary ammonium group derived from a tertiary amine hapten, preferably one of the drugs depicted in Table 1 which does not require derivatization in order to have tertiary amine fucntionality, L is a linker having 1–10 atoms, such as —CH$_2$—, and Z is a C=O group, and x is greater than or equal to one, preferably greater than one, and B— is preferably I⁻ or Br⁻. The following are examples of preferred quaternary ammonium conjugates:

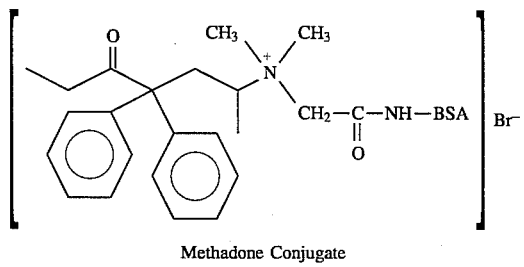

Methadone Conjugate

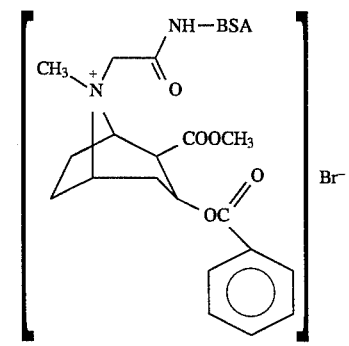

Cocaine Conjugate

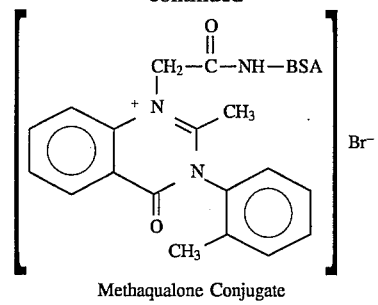

Methaqualone Conjugate

The above conjugates illustrate use of the amide linkage to link a quaternary ammonium hapten having the linker, CH$_2$, where the residue, Z, is C=O and the NH shown is derived from the amine group of the carrier.

Preferably, the quaternary hapten derivative is ammonium coupled to the carrier under known conditions normally used to form amide linkages. The quaternary ammonium hapten derivative can be reacted with a linking group having a having carboxyl group, such as ethyl bromoactetate (BrCH$_2$CO$_2$C$_2$H$_5$) for linking with the amine group of the carrier.

Other linkages between the linking group and the carrier, such as imine, diazo, alkyl, urea, thiourea, carbamate and thiocarbamate linkages can also be prepared using known conditions and procedures.

Quaternary ammonium conjugates in which the carrier is a reporter such as a latex particle, can be prepared by first derivatizing a tertiary hapten or hapten derivative by attaching an appropriate bifunctional linking group as described above and then attaching the linking group via its reactive group to a functional group on the particle.

Alternatively, the reporter particle reagent of the present invention can be prepared by directly reacting a tertiary amine hapten or hapten derivative having a tertiary amine functionality, with a particle having suitable functional groups for linking with the tertiary amine of the or hapten derivative thereof. For example, U.S. Pat. No. 4,480,042 issued to Craig et al. hereby incorporated by reference, disclose polystyrene/polyglycidyl methacrylate latex particles which can be directly linked with the tertiary amine of the hapten or hapten derivative thereof. The linking reaction involving the alkylation of amines by epoxides using known methodology, is shown below:

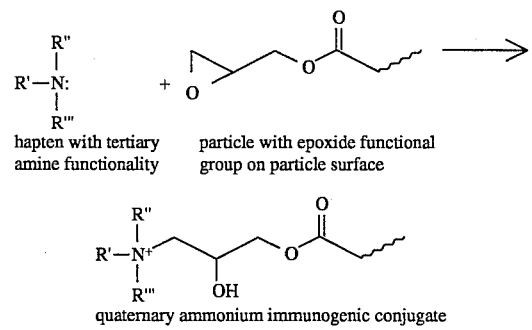

The quaternary ammonium conjugates of the present invention can be used to elicit antibodies using known antibody producing and screening procedures. The immunogen can be injected into appropriate animal hosts to stimulate the production of antibodies. The antibodies so produced can be harvested for direct use in specific binding reactions with the hapten or closely related analogs, or they can be first purified from animal serum by any of several known means such as affinity chromatography. Alternatively the immune lymphocytes harvested from the injected host can be screened using the conjugates of this invention to select those cells which are responsive to the quaternary ammonium conjugate. These can then be fused with appropriate myeloma cells, to produce hybridomas that are capable of producing monoclonal antibodies. Methods of cell fusion, selection and proliferation are well known and are generally modifications to the procedures of Kohler et al., Nature, vol. 256, 495–497 (1975).

It is known that the nature of the binding between the hapten and carrier of an immunogenic conjugate can affect the ability of the conjugate to elicit antibodies suitable for the detection of the hapten. Surprisingly, the quaternary ammonium immunogenic conjugates of the present invention are capable of raising antibodies of suitably high specificity for the detection and/or quantitation of a hapten of interest.

The conjugates of the present invention can be used in immunoassays for determining a hapten. For example, immunoassays can be performed with the quaternary ammonium immunogenic conjugate of the present invention in which the immunogenic conjugate is allowed to compete with an unknown hapten for binding sites on an antibody against the hapten. The immunogenic conjugate can be immobilized on a solid phase or the specific binding reactions can occur in solution. When a separation of unreacted reagent(s) is desired, the reactions are most easily performed with the immunogenic conjugate immobilized on a solid phase.

Immunoassays employing the immunogenic conjugates of the present invention can also be performed in a non-competitive format using an excess of labeled specific antibody to react with the unknown hapten. In this approach the quaternary ammonium conjugate is attached to a solid support and used to remove any unbound labeled specific antibody. The amount of label remaining in solution or bound to the solid phase can be measured as an indication of the amount of unknown hapten present.

The quaternary ammonium immunogenic conjugates of the present invention include conjugates of haptens with non-immunogenic carriers such as reporter compounds, and can include, for example: reporter reagents which are fluorescence-tagged, chemiluminescent, or enzyme labeled quaternary immunogenic conjugates. Such reporter-labeled reagents can be utilized to detect and/or quantitate a hapten in a test sample using any known immunoassay format. Such known immunoassay formats include heterogeneous and homogeneous, competitive and non-competitive formats.

The immunogenic conjugates of the present invention can be utilized to elicit antibodies which can, in turn, be used in any known immunoassay format employing specific binding reactions. The antibodies of the present invention are prepared against the quaternary immunogenic conjugates as described above and can be utilized in any known immunoassay format. Such immunoassays can be carried out in various test samples of biological fluids, including for example, serum, plasma, blood, urine, and saliva. Immunoassays utilizing antibodies prepared against the quaternary ammonium immunogenic conjugates of the present invention can have several known formats and can be heterogeneous or homogeneous, competitive or non-competitive. Examples of suitable immunoassays include known ELISA or enzyme linked immunosorbent immunoassays, sandwich immunoassays, fluorescence polarization immunoassays, nephelometric assays, and particle-based agglutination immunoassays such as those employing latex particles. The antibodies employed can be labeled with reporters such as enzymes or utilized without further modification.

In a particle based agglutination assay the change in turbidity caused by particle agglutination or its inhibition is measured. Quaternary ammonium immunogenic conjugates which are latex particle reagents can be prepared as described above and the agglutination or inhibition of the reaction of these particle reagents with agglutinating agents such as a hapten in a test sample antibodies potentiometrically determined. The reaction can be performed by direct competition between the particle reagents and the hapten or by sequential reaction of the hapten with antibody followed by addition of the particle reagent.

The following examples illustrate the invention.

EXAMPLE 1

Preparation of a Quaternary Ammonium Methadone Hapten For An Immunogenic Conjugate A. Preparation of Methadone (free base)

Methadone (free base) was prepared for step B below by dissolving 10 grams of methadone hydrochloride in 100 mL of warm water at approximately 50° C. and crystallizing the free base out of solution by slowly adding 20 mL of a saturated aqueous potassium carbonate solution, pH 12.2 to the methadone hydrochloride solution with stirring. After crystallization was complete, the methadone crystals were filtered and redissolved in about 75 mL ethanol (ETOH). Following this the methadone was precipitated by the addition of 200 mL of water. The precipitate was filtered and dried in vacuo. The resulting yield of methadone was 8.79 g methadone or approximately 98%.

B. Preparation of N-Carboxymethyl Methadone Ethyl Ester Bromide

N-carboxymethyl methadone ethyl ester bromide was prepared as follows:

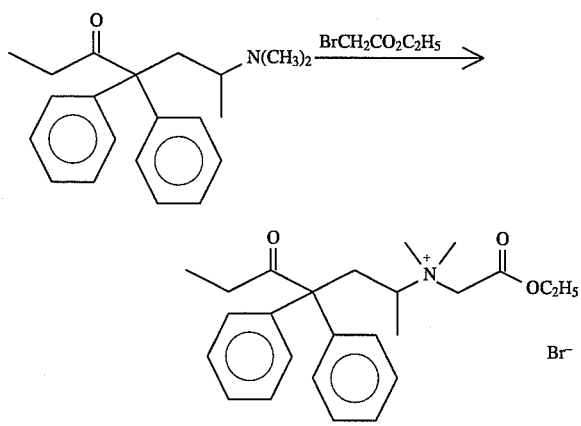

To 3.1 g of methadone (free base) prepared as described above in step A. was added 1.11 mL of ethyl bromoacetate which had been dissolved in 10 mL of warm (approximately 40° C.) ethyl acetate. The mixture was allowed to react overnight at room temperature to produce the tertiary amine derivative N-carboxymethyl methadone ethyl ester bromide. The mixture was then heated to 60° C. and maintained at this temperature for 1 hour. The heated mixture was then mixed with 10 mL of ether, and the solid N-carboxymethyl methadone ethyl ester bromide was filtered, and washed with approximately 30 mL of ether. The N-carboxymethyl methadone ethyl ester bromide was then dried in vacuo for 5 hours. The yield of N-carboxymethyl methadone ethyl ester bromide was 4.887 g or approximately 100%.

C. Preparation of N-Carboxymethyl Methadone Bromide (CMM)

A quaternary ammonium derivative of methadone useful in preparing an immunogenic conjugate for an immunoassay for methadone, N-carboxymethyl methadone bromide (CMM), was prepared as follows:

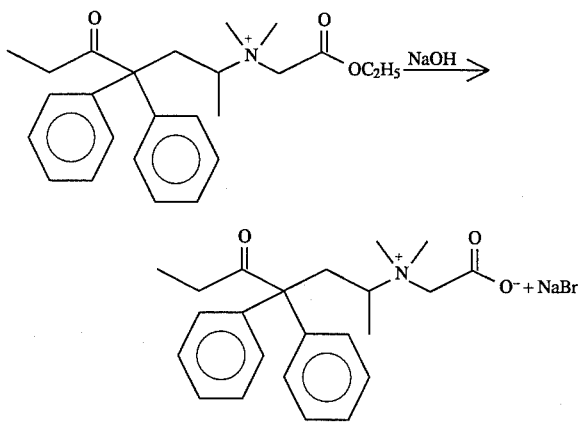

The quaternary ammonium derivative N-carboxymethyl methadone ethyl ester bromide prepared in Step B. above was mixed with 2 mL of 5M sodium hydroxide (NaOH) and 15 mL of water. This mixture was then heated for 5 hours at 50° C. During heating, the initially solid N-carboxymethyl methadone ethyl ester bromide dissolved. The resulting solution was then frozen and lyophilized. The equivalent weight of the N-carboxymethyl methadone bromide, i.e., without separation of sodium bromide was 460 g. The yield of N-carboxymethyl methadone bromide was 4.21 g or approximately 91.6%.

EXAMPLE 2

Preparation of An Immunogenic Conjugate of A Quaternary Ammonium Derivative of Methadone An immunogenic conjugate of a quaternary ammonium derivative of methadone and an immunogenic carrier, Keyhole Limpit Hemocyanin (KLH), was prepared using the following procedure.

N-carboxymethyl methadone/KLH Immunogenic conjugate was prepared as follows:

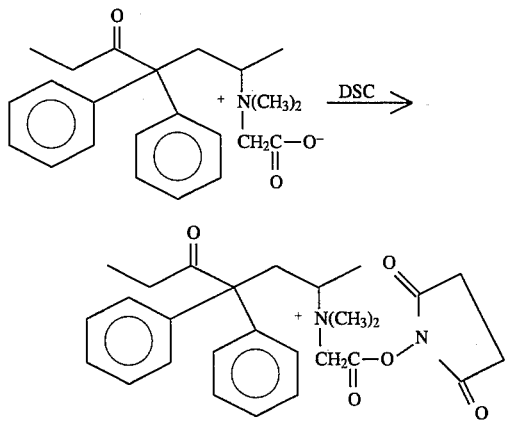

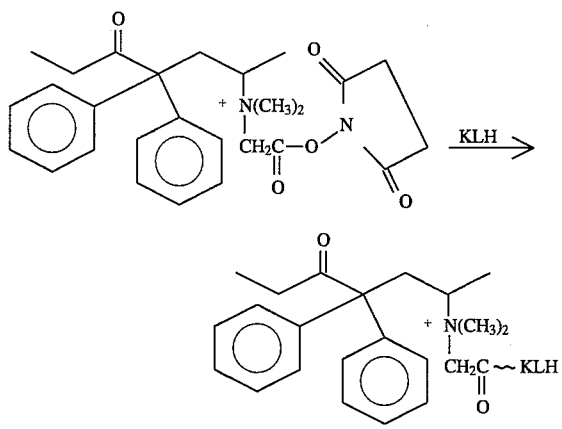

An amount of 179 mg of disuccinimidyl carbonate (DSC) was dissolved in 3 mL of dry dimethylsulfoxide (DMSO) to prepare a 0.5 mM solution of DSC in DMSO. The DSC solution was added to 138 mg of a mixture containing a 1:1 molar ratio of CMM and NaBr dissolved in 3 mL of DMSO (0.3 mM solution of the CMM and NaBr mixture in DMSO). The CMM was prepared using the procedure described above in Example 1. The reaction mixture was allowed to stand for 1 hour.

A volume of 1.6 mL of the product reaction mixture was added with stirring to a solution of 50 mg of the immunogenic protein carrier keyhole limpit hemocyanin (KLH) dissolved in 10 mL of water. The resulting mixture was allowed to stand undisturbed for 3.5 hours and then dialyzed over night against 10 L of water.

EXAMPLE 3

Preparation of An Anti-Methadone Monoclonal Antibody Raised Against A Quaternary Ammonium Methadone Immunogenic Conjugate Standard hybridoma techniques were used for the preparation of antibody producing hybridoma cells. The immunogenic conjugate N-carboxymethyl methadone/KLH conjugate prepared as described above Example 2 was injected into host mice to elicit an antibody production, the spleen cells from the injected mice were then fused with myeloma cells to generate antibody producing hybridomas, and an antibody against methadone was selectively screened and for use in an immunoassay for methadone. The process used was substantially the same as that described by Geltosky in U.S. Pat. No. 4,524,025 and by Kohler and Milstein, Nature, vol. 256, 495–497 (1975).

EXAMPLE 4

Inhibition Assay for Methadone Using An Anti-Methadone Monoclonal Antibody Prepared From A Quaternary Ammonium Methadone Immunogenic Conjugate Immulon II 96 well polystyrene microtiter plate wells (Dynatec, U.S.A.) were coated with 50 μL each of a methadone/ovalbumin immunogenic conjugate at a concentration of 5 μg/ml in phosphate buffered saline (PBS) (Sigma Chemical Co., Milwaukee, Wis.) pH 7.2 and allowed to incubate overnight for about 18 hours at room temperature. The plates were then washed three times with PBS, pH 7.2.

An amount of 200 µL of PBS containing 3% fraction V BSA (Sigma Chemical Co., Wisconsin, U.S.A.), pH 7.2 was added to each well and allowed to incubate for 120 minutes at room temperature. This treatment blocked any remaining adsorptive sites in plate wells not occupied by the conjugate to prevent the nonspecific adsorption of reagents subsequently added. The plates were then washed three times with PBS pH 7.2 and stored at 4° C. temperature until used.

An inhibition immunoassay was performed at room temperature. An assay buffer was used containing of 3% BSA in PBS and 0.05% GAFAC™ (GAF Corp., U.S.A.) pH 7.2. (Other detergents such as Triton X-100 (Rohm and Haas Corp., Pa., U.S.A.) can also be used in place of GAFAC). The anti-methadone antibody prepared as described above in Example 3 was diluted approximately 1:10 in the assay buffer. An amount of 50 µL of the diluted anti-methadone antibody was premixed with an equal volume of aqueous methadone hydrochloride at a concentration of in the same assay buffer. An amount of 75 µL of this mixture was then transferred to each well of the coated microtitre plate, and incubated at room temperature for one hour. The mixture was then removed by washing three times with PBS pH 7.2, followed by the addition of 100 µL of Goat-antimouse/horse radish peroxidase (HRP) conjugate (Zymed Laboratories, Inc., San Francisco Calif.). The plates were incubated at room temperature for 1 hour. The HRP conjugate was then removed by washing with assay buffer and 100 µL of a stock solution of a chromogenic substrate, ABTS (Kirkegaard and Perry Laboratories in Gaithersburg, Md., U.S.A.) was added to each microtitre plate well and allowed to incubate at room temperature for 30 minutes. The resulting change in optical density was measured using a microtiter plate reader at a wavelength range of 405–490 nm. The results of the inhibition assay for methadone are shown below in Table 2.

TABLE 2

Methadone Inhibition of Anti-Methadone Binding To Methadone/ovalbumin Immunogenic Conjugate

| Methadone (ng/mL) | Optical Density (mAU) |
| --- | --- |
| 0.00 | 421 |
| 0.17 | 438 |
| 0.51 | 425 |
| 1.52 | 433 |
| 4.57 | 414 |
| 13.70 | 380 |
| 41.20 | 343 |
| 124.00 | 255 |
| 370.00 | 147 |
| 1111.00 | 65 |
| 3333.00 | 35 |

The results in Table 2 indicate that anti-methadone antibodies raised against N-carboxymethyl methadone/KLH immunogenic conjugates will bind to a methadone/ovalbumin immunogenic conjugate immobilized on a solid phase, and that the quaternary ammonium conjugates of the present invention are useful in immunoassays for methadone.

EXAMPLE 5

Preparation of A Quaternary Ammonium Latex Methadone Particle Reagent

An amount of 400 µl of a 0.2M methadone hydrochloride (Sigma Chemical Co., Wisconsin, U.S.A.) aqueous solution was as added to a mixture containing 200 µl of 0.1M aqueous solution of ethylenedioxydiethylamine (Fluka Chemical Co., U.S.A.) and 4.4 ml of 40 mM sodium tetraborate decahydrate (Sigma Chemical Co., Wisconsin, U.S.A.) containing 2.2% Rhodofac RE-610 (Rhone Poulenc Corp., N.J., U.S.A). To the resulting suspension was added 5 ml of a 20% solids mixture of 60 nm polystyrene/polyglycidyl methacrylate latex particles. The particles were prepared using a procedure substantially similar to that disclosed in U.S. Pat. No. 4,480,042 issued Oct. 30, 1984 to Craig et al., hereby incorporated by reference. The mixture was heated at 70° C. for 18 hours and then diluted with 10 ml of a wash buffer composed of 150 mM phosphate buffer at pH 7.8 with 0.5% Rhodofac. The mixture was centrifuged at 28,000 rpm in a RC-28S Sorval® Centrifuge (E. I. du Pont de Nemours and Company, Delaware, U.S.A.). The supernatant was discarded and the pellet was resuspended in 20 ml wash buffer with the aid of a sonicator. The centrifugation and resuspension steps were repeated an additional three times.

EXAMPLE 6

Immunoassay Using Quaternary Ammonium Methadone Latex Particle Reagent

An assay buffer was prepared containing 2.62 g/l monobasic sodium phosphate monohydrate, 11.5 g/l anhydrous dibasic sodium phosphate, 0.6% Rhodofac and 3% PEG 8000 and adjusting the pH to 7.2. The latex particles prepared as described above were diluted 1:50 in the assay buffer to produce a latex reagent solution.

A stock solution was prepared containing 160 µg/ml of purified monoclonal antibody against methadone preared using hybridoma techniques known in the art in 150 mM sodium chloride, 100 mM sodium phosphate, and 1% BSA at pH 5.5.

Calibrator solutions of methadone hydrochloride were prepared by diluting 1 mg/ml concentrate of methadone hydrochloride in water into a buffer containing 15 mM sodium phosphate buffer containing 0.35% Rhodofac.

The assay was performed using a Cobas Bio diagnostic instrument (Roche Diagnostics, New Jersey, U.S.A). The instrument was programmed to mix 3 µl of calibrator solution prepared as described above, with 150 µl of the latex reagent solution prepared as described above, and 51 µl of water. This mixture was incubated for 30 seconds to bring it up to 37° C., followed by the addition of 20 µl of the purified monoclonal antibody solution as described above. The change in optical density was recorded after 240 seconds of reaction time. The results are shown in Table 3 below.

TABLE 3

| Methadone (µg/ml) | Change in Optical Density (milli-absorbance) |
| --- | --- |
| 0 | 483 |
| 0.5 | 453 |
| 1.0 | 393 |
| 2.5 | 356 |
| 5.0 | 259 |
| 10 | 145 |
| 25 | 44.5 |
| 50 | 22 |

The results in Table 3 indicate free methadone competes with the immunogenic conjugate or methadone particle reagent for binding with the anti-methadone antibody, such that the presence of free methadone results in a decrease or inhibition of particle agglutination, and that the methadone particle reagent used is useful as a reagent in a particle agglutination immunoassay for the determination of methadone.

What is claimed is:

1. A quaternary ammonium conjugate useful for eliciting antibodies to a non-quaternary ammonium hapten or in an immunoassay for determining the presence and/or amount in a test sample of a non-quaternary ammonium hapten, the quaternary ammonium conjugate comprising compounds of the formula:

$$((Q^+\text{---}L\text{---}Z)_x\text{---}M) \ B^-$$

wherein $Q^+$ is a quaternary ammonium group, cyclic or acyclic, derived by covalent attachment of a linker to a hapten selected from the group consisting of cocaine, methadone, methaqualone, propoxyphenes, phencyclidine, amphetamine, benzodiazepams, quinidine, procanimide, N-acetyl procanimide, and tricyclic amines;

L is a linker comprising from 0 to 20 carbon atoms and heteroatoms arranged in a straight or branched chain and/or containing ring structures, with no more than a total of 6 heteroatoms and with no more than two heteroatoms linked in sequence;

$Q^+$ is linked to L at the tertiary amine group of the hapten;

—Z— is a residue group selected from the group consisting of —C=O, —CH=, —N=N—, —NH—, —NCH$_3$, —NH—S=C, —SO$_2$—, —O—C=O, and —C=O—NH—NH$_2$—;

x is greater than or equal to 1;

M is a carrier selected from the group consisting of poly(amino)acids, carbohydrates, yeasts, polysaccharides and solid phase particles;

$B^-$ is an anion; and $(Q^+\text{---}L\text{---}Z)_x\text{---}$ is covalently bound to M.

2. The quaternary ammonium conjugate of claim 1 wherein the linker is selected from the group consisting of —CH$_2$CO— and —CH$_2$COHCO—.

3. A quaternary ammonium conjugate prepared by a process which comprises:

coupling a quaternary ammonium hapten to a carrier, the carrier selected from the group consisting of poly(amino)acids, carbohydrates, yeasts, polysaccharides, and solid phase particles, the quaternary ammonium hapten obtained by attaching a bifunctional linking group to a hapten selected from the group consisting of cocaine, methadone, methaqualone, propoxyphenes, phencyclidine, amphetamine, benzodiazepams, quinidine, procanimide, N-acetyl-procanimide, and tricyclic amines, the bifunctional linking group covalently bindable to the carrier and comprising from 0 to 20 carbon atoms and heteroatoms arranged in a straight or branched chain and/or containing ring structures, with no more than a total of 6 heteroatoms and no more than two heteroatoms linked in sequence.

4. The quaternary ammonium conjugate according to claim 3 wherein the bifunctional linking group comprises a reactive group selected frown the group consisting of —CO$_2$H, —NH$_2$, —NCO, —CONHNH$_2$, —CNOR, —CHO, —Br, —I, —NCS, —OCOCl, —SO$_2$Cl, —OCSCl, and —NHCH$_3$.

5. A solid phase immunoassay for detecting the presence and/or amount of a non-quaternary ammonium hapten comprising the steps of (1) immobilizing the immunogenic conjugate of claim 1 or 5 on a solid phase;

(2) incubating (a) a sample containing an unknown concentration of a non-quaternary ammonium hapten with (b) an antibody raised against the quaternary ammonium conjugate of claims 1 or 5 and reactive with the corresponding non-quaternary ammonium hapten;

(3) incubating the mixture of the product of step (2) with the immobilized conjugate of step (1);

(4) separating liquid phase from the solid phase of step (3);

(5) detecting either the bound free antibody in the separated liquid phase;

(6) correlating the detection signal to the amount or presence of the non-quaternary ammonium hapten.

6. The quaternary ammonium conjugate of claim 1 wherein the carrier is a latex particle.

7. A particle agglutination immunoassay for determining the amount or presence of a non-quaternary ammonium hapten in a test sample which comprises:

(1) incubating a mixture of the quaternary ammonium conjugate of claim 10, the test sample, and an antibody prepared from the conjugate of claim 3;

(2) measuring increased particle size resulting from step (1); and (3) correlating the increased particle size with the amount or presence of non-quaternary ammonium hapten in a test sample.

8. The solid phase immunoassay of claim 5 wherein the antibody incubated in step (2) is labeled with a tag selected from the group consisting of a radioisotope, a chemiluminescent compound, a fluorophore, or an enzyme.

9. The solid phase immunoassay of claim 5 wherein the incubating steps (2) and (3) occur simultaneously.

10. The particle agglutination immunoassay of claim 7 wherein the mixture is formed either by (1) combining the quaternary ammonium conjugate of claim 6 with the test sample and then adding to that mixture, or (2) combining the antibody with the test sample and then adding to that mixture the quaternary ammoniun conjugate.

* * * * *